United States Patent [19]

Akaike et al.

[11] Patent Number: 5,061,247
[45] Date of Patent: Oct. 29, 1991

[54] GASKET AND MEDICAL DEVICE USING THE SAME

[75] Inventors: Yoshiaki Akaike, Yamanashi; Yoshinori Nishiya, Yokkaichi, both of Japan

[73] Assignee: Terumo Kabushiki Kaisha, Tokyo, Japan

[21] Appl. No.: 445,534

[22] Filed: Dec. 4, 1989

[30] Foreign Application Priority Data

Dec. 9, 1988 [JP] Japan .................. 63-310196

[51] Int. Cl.⁵ .............................................. A61M 5/00
[52] U.S. Cl. .................................... 604/187; 604/218
[58] Field of Search ............... 604/191, 187, 222, 218

[56] References Cited

U.S. PATENT DOCUMENTS

| 3,714,943 | 2/1973 | Yanof et al. | 604/191 |
| 4,048,255 | 9/1977 | Hillier et al. | 604/222 |
| 4,303,070 | 12/1981 | Ichikawa et al. | 604/222 |
| 4,704,105 | 11/1987 | Adorján et al. | 604/222 |

Primary Examiner—Stephen C. Pellagrino
Assistant Examiner—Michael Rafa
Attorney, Agent, or Firm—Frishauf, Holtz, Goodman & Woodward

[57] ABSTRACT

A gasket is made of a composite comprising hydrogen-added derivative (component a) of a styrenebutadiene block copolymer, a plasticizer (component b), and a polyethylene resin having a density of 0.940 g/cm³ or more (component c). A medical device includes a cylindrical body and a gasket capable of moving in close contact with the inner surface of the cylindrical body. The gasket of the medical device is the same of the aforesaid type of the gasket.

18 Claims, 3 Drawing Sheets

EXAMPLE 1

START 10MIN 20MIN 30MIN 40MIN 50MIN 60MIN

EXAMPLE 3

EXAMPLE 6

COMPARATIVE EXAMPLE 12

GASKET AND MEDICAL DEVICE USING THE SAME

BACKGROUND OF THE INVENTION

The present invention relates to a gasket and a medical device using the same.

Known are medical devices such as disposable injectors each of which comprises a cylindrical body and a gasket which can move in close contact with the inner surface of the cylindrical body.

Conventionally, the above-described gasket is made of, as disclosed in Japanese Patent Publication No. 59-18427 U.S. Pat. No. 4,303,070, vulcanized rubber or styrene type thermoplastic elastomer (to be called "TPE" hereinafter). The styrene type TPE is made of a composite consisting of hydrogen-added derivative of styrene-butadiene block copolymer, plasticizer, and polypropylene for improving workability and for adjusting the hardness.

A large facility is needed to manufacture the gasket made of vulcanized rubber since such a gasket is manufactured after it has been subjected to a complicated vulcanization process. Furthermore, a variety of additives such as sulfur, a vulcanization accelerator, and a filler are necessary. As a result, there is a fear of an elution of the additives into the liquid medicine when the medical device is used.

On the contrary, although the gasket made of the styrene TPE exhibits an advantage in the formability at the time of the injection molding and another advantage in that the fear of elution of sulfur can be eliminated, it is disadvantageous relative to vulcanized rubber in terms of the elasticity of the rubber, where the term "the elasticity of rubber" means in particular the tensile characteristics whereby that the inflection points such as the yielding points are reduced much as possible and also the modulus (for example, the stress when expanded by 300%) is at a relatively high level in relation to the hardness. That is, in the styrene TPE, polypropylene which is the component which causes the inflection point such as the yield point to be generated also causes the modulus to be lowered in the tensile characteristics. Therefore, in a case where the gasket made of the styrene TPE is employed in an injector, the displacement added to a portion to be pushed does not immediately correspond to the distance of movement of the gasket. Therefore, a problem arises in that the gasket intermittently moves; that is, a so-called pulsation phenomenon takes place.

An object of the present invention is to provide a gasket and a medical device using the same, the gasket exhibiting an excellent formability and safety against elution and being capable of preventing pulsation phenomenon.

SUMMARY OF THE INVENTION

A gasket in accordance with the present invention in one embodiment is made of a composite comprising a hydrogen-added derivative (component a) of styrene-butadiene block copolymer, a plasticizer (component b), and a polyethylene resin having a density of 0.940 g/cm³ or more (component c).

A gasket in accordance with the present invention in another embodiment includes a composite which is formed by mixing 100 parts by weight of the component a and the component b with 10 to 50 parts by weight of the component c, the 100 parts being the total of the component a by 40 to 60 wt % and the component b by 60 to 40 wt %.

A gasket in accordance with the present invention in a further embodiment is made of a composite comprising a hydrogen-added derivative (component a) of styrene-butadiene block copolymer, a plasticizer (component b), a polyethylene resin having a density of 0.940 g/cm³ or more (component c), and a hydrocarbon-type wax (component d).

A gasket in accordance with the present invention in still a further embodiment includes composite which is formed by mixing 100 parts by weight in total of the component a and the component b with 10 to 50 parts by weight of the component c, and 2 to 20 parts by weight of the component d, the 100 parts being the total of the component a by 40 to 60 wt % and the component b by 60 to 40 wt %.

A medical device in accordance with the present invention in an embodiment comprises a cylindrical body and a gasket arranged in close contact with the inner surface of the cylindrical body and adapted to slide therein, the gasket being one obtained in accordance with any one of the aforesaid embodiments.

The components and mixture proportions of the composite forming the gasket of this invention will now be described in detail.

Composite a

The above-described component a used in this invention is a hydrogen added derivative of a copolymer which is expressed by the general formula:

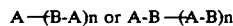

[where A represents a polymer block of styrene, B represents a polymer block of butadiene, and n represents an integer ranged between 1 and 5].

In order to maintain the elastomer characteristics, it is desirable that the polymer block B employ a polymerization condition in which the proportion of the 1,2-micro structure in the micro structures in polybutadiene is 20 to 50%, and in particular, a polymerization condition in which the proportion of the 1,2-micro structure is 35 to 45%. Further, it is desirable that the proportion of the polymer block B in the above-mentioned copolymer be at least 65 wt %.

The number average molecular weight of the hydrogen-added block copolymer constituting the above component a is preferably in the range of 5,000 to 1,000,000, more preferably, in the range of 10,000 to 800,000, and still more preferably, in the range of 30,000 to 500,000. Its molecular weight distribution, that is, the ratio of its weight average molecular weight (Mw) to its number average molecular weight (Mn):(Mw/Mn) is 10 or less. Further, the molecular structure of the hydrogen-added block copolymer may be a straight-chain structure, a branch structure, or a radial structure, or an arbitrary combination of these structures.

These block copolymers may be manufactured by any manufacturing method as long as the above structure can be obtained. The hydrogen-added block copolymer used in this invention can be synthesized, for example, by first synthesizing a styrene-butadiene block copolymer in an inactive solvent using a lithium catalyst or the like in accordance with the method disclosed in Japanese Patent Publication No. 40-23798, and then adding hydrogen to the block copolymer thus obtained in an inactive solvent in the presence of a hydrogen-adding catalyst in accordance with the method disclosed in Japanese Patent Publication No. 42-8704, 43-6636, or the methods disclosed in Japanese Patent Laid-Open Publication Nos. 59-133203 and 60-79005.

It is preferable that the addition of hydrogen in the manufacturing process for the block copolymer for the component a of this invention is conducted such that hydrogen is added at least 50%, preferably 80% or more of the olefinic linkages in the polymer block B and hydrogen is also added to 25% or less of the aromatic unsaturated bonds in the polymer block A. As the block polymer of this type, a polymer on the market such as KRATON-G (the trade name of a polymer manufactured by Shell Chemical) can be used.

Component b

It is preferable that a mineral oil type or synthetic resin plasticizer is used as the component b which is the softener for according to the present invention.

The mineral type plasticizer is a mixture consisting of aromatic rings, naphthene rings, and paraffin chains. The plasticizer is classified such that the mixture in which the number of carbons in the paraffin chains exceeds 50% is called a paraffin type plasticizer, the mixture in which the same in the naphthene rings ranges between 30 and 45% is called a naphthene type plasticizer, and the mixture in which the number of the aromaic carbons exceeds 30% is called an aromatic type plasticizer. The preferable mineral type plasticizers as the component b of the present invention are the naphthene type plasticizer and the paraffin type plasticizer in which the proportion of the aromatic hydrocarbon thereof is less than 30%. The aromatic plasticizer is not preferably used in terms of dispersion characteristics with respect to the above-described component a according to the present invention.

The properties of the mineral type plasticizer are arranged such that the coefficient of kinetic viscosity at 37.8° C. is 20 to 500 cst, the pour point is −10° to −15° C., and the flash point (COC) is 170° to 300° C.

Although polybutene, low molecular weight polybutadiene, or the like can be used, the mineral type plasticizer is preferably used.

Component C

The polyethylene resin of the above-mentioned component c is a high-density polyethylene resin with a density of 0.940 g/cm$^3$ or more and can be obtained by the normal method (the low-pressure polymerization method). The MFR adopted is 0.1 to 50 g/10 min at 190° C. under a load of 2.16 kgw.

Normally, in addition to a plasticizer, a resin component (e.g., polypropylene) is generally added to a thermoplastic elastomer based on a styrene-butadiene copolymer with a view to adjusting its hardness and workability. This invention is characterized in that a certain amount of polyethylene resin is added as this resin component.

The melting point of a polypropylene resin (about 160° C.) is higher than that of a polyethylene resin (about 120° C.). Further, a polypropylene resin exhibits a higher modulus of flexural elasticity. Under the circumstances, it has been believed that a thermoplastic elastomer having a satisfactory heat resistance and rubber elasticity can be obtained by using a polypropylene resin. However, the inventors of this invention has found out that, by using, instead of a polypropylene resin, a polyethylene resin with a density of 0.940 g/cm$^3$ or more, a substantial improvement in rubber elasticity and heat resistance can be attained. A polyethylene resin density of less than 0.940 g/cm$^3$ results in excessive bleeding of the plasticizer and insufficient heat resistance (permanent compression strain).

Componet

The hydrocarbon-type wax constituting the component d used in this invention for the purpose of improving the workability (fluidity and mold appearance) may be a paraffin wax obtained through petroleum refining and exhibiting a melting point of 40° to 100° C. and a 100° C. viscosity of 1 to 30 cSt or a polyethylene-type wax obtained through polymerization and exhibiting a dropping point (ASTM-D-3104) of 90° to 120° C. and a 140° C. viscosity (Brooksfield) of 40 to 7,000 cps. A hydrocarbon-type wax preferable as the component d of this invention may be a polyetylene-type wax.

Mixture and Kneading

The mixture proportion of the components constituting the TPE (thermoplastic elastomer) of this invention may be such that the proportion of the component a with respect to the total amount of the component b is 40 to 60 wt %, preferably, 40 to 55 wt %. If the proportion is less than 40 wt %, the rubber elasticity and heat resistance of the TPE obtained will be rather poor, with the bleeding of the plasticizer being deteriorated. If it is more than 60 wt %, the flexibility, formability and workability of the TPE will be deteriorated. The proportion of the component b is to be 60 to 40 wt %, preferably, 60 to 45 wt %. If the proportion is more than 70 wt %, the rubber elasticity and heat resistance of the TPE will be rather poor, with the bleed-out of the plasticizer being deteriorated. If it is less than 40 wt %, the flexibility, formability and workability of the TPE will be deteriorated.

The proportion of the component c to 100 parts by weight of the sum total of the components a and b is to be 10 to 50 parts by weight, preferably, 10 to 30 parts by weight. If the proportion is less than 10 parts by weight, the formability and workability will be poor; if it is more than 50 parts by weight, the flexibility of the TPE will be lost, and, at the same time, the bleed-out of the plasticizer will deteriorate.

The proportion of the component d, which is used in this invention for the purpose of improving the workability (fluidity and mold appearance), is to be 2 to 20 parts by weight, preferably 3 to 10 parts by weight, with respect to 100 parts by weight of the sum total of the components a and b. If the proportion is less than 2 parts by weight, the resulting mold appearance will be an unsatisfactory one; if it is more than 20 parts by weight, the flexibility and rubber elasticity of the TPE will deteriorate.

While the present invention is characterized in that these necessary components are contained by a certain quantity when obtaining TPE, an additional component such as a polyolefine polymer, a polystyrene polymer, or an inorganic filler may be added in a range which does not involve deterioration in the basic performance of the invention, the inorganic filler including calcium carbonate, talc, mica, and carbon black. Furthermore, in order to meet the aiming property, additives such as an antioxidant, ultraviolet absorber, slipping agent, and fluidity accelerator may be added.

The TPE according to the present invention can be manufactured by a mechanical melt kneading process. Specifically, a usual mechanical melt kneader such as a Banbury mixer, various kneaders, a single or two-shaft extruder can be used.

The TPE according to the present invention may be formed by the method of molding thermoplastic resin such as the injection molding, extrusion molding, and blow molding.

Thus, the TPE forming the gasket of this invention contains, instead of the polypropylene constituting the conventional styrene-type TPE described above, a polyethylene resin having a density of 0.940 g/cm$^3$ or more, thereby making it possible to secure satisfactory formability and safety against elution without spoiling the rubber elasticity which is inherent in a hydrogen-added derivative of styrene-butadiene block copolymer. As a result, a gasket and a medical device using the same which exhibits an excellent formability and safety against elution without any problem of pulsation phenomenon can be obtained.

DETAILED DESCRIPTION

Figure 1:
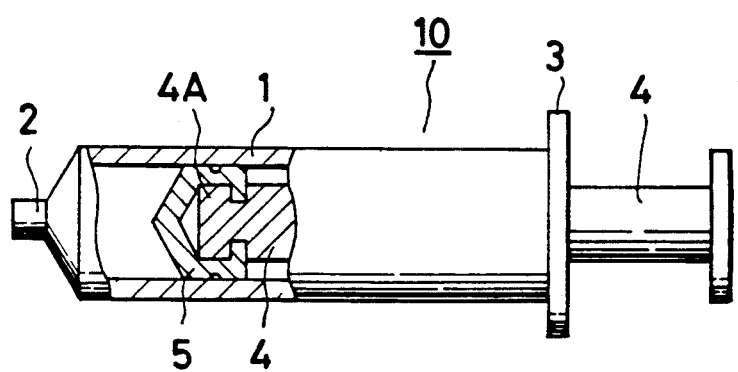
FIG. 1 is a schematic view of an injector in which the gasket according to the present invention is used, and FIG. 2 (a) is a perspective view depicting a pulsation system.

In an injector 10 shown in FIG. 1, reference numeral 1 represents a syringe made of hard synthetic resin, 2 represents a nozzle, and 3 represents a flange. Reference numeral 4 represents a body to be pushed which is made of hard synthetic resin, and 5 represents a gasket according to the present invention which is fitted to a front portion 4A to be engaged by the body 4 to be pushed.

In the following embodiments and comparative examples, the testing methods for making various evaluations were as follows, where a test sample was a 2 mm-thickness sheet (sample for the following tests (1) to (3)) manufactured by a 5-ounce in-line screw type injection molding machine under the conditions that the injection pressure was 500 kgf/cm$^2$, injection temperature was 220° C., and the temperature of the mold was 40° C. Furthermore, another test sample was a gasket for 5 ml syringe having the peak diameter of 13.2 mm (sample for the following tests (4) to (7). The inner diameter of the outer cylinder for a 5 ml-syringe was 13.0 mm.

(1) JIS-A hardness . . . JISK-6301

If the gasket for a cylinder is too hard, the sliding ability is insufficient and the assembling of it is difficult. On the contrary, if it is too soft, it cannot be strongly engaged to the body to be pushed, causing the separation of them to occur. It is preferable that the hardness is ranges between 20 or more and 85 or less.

(2) Stress when compressed by 300% (kgf/cm$^2$) . . . JISK-6301

In the relationship with hardness, the higher the stress when compressed by 300% becomes, the pulsation can be prevented. When the stress when compressed by 300% becomes 22 to 25 kgf/cm$^2$ under the condition that the hardness is 68 to 65, the pulsation is caused to occur.

(3) Permanent compression strain (%) . . . JISK-6301 (70° C.×22 hours)

The permanent compression strain was measured by inserting the gasket into the cylinder of the syringe 1 and leaving it in this condition. For the sealing property to be maintained, it is desirable that the compression set be as small as possible. An appropriate compression set value is in the range of 60% or less.

(4) Formability

Was evaluated from the fluidity when performing injection molding.

(5) Mold Appearance

Was evaluated from the flow marks on the mold surface.

(6) Pulsation

Figure 2A:
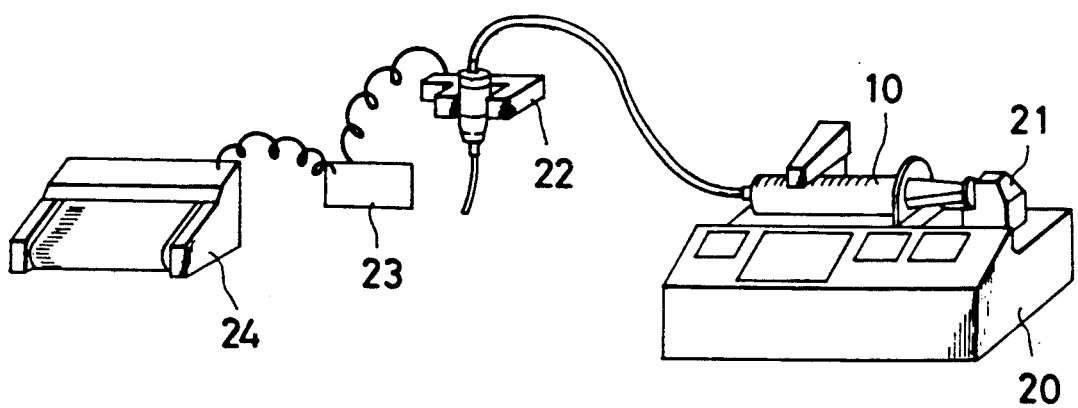
FIG. 2(b) is a diagram which illustrates the results of a pulsation test.
Figure 2B:
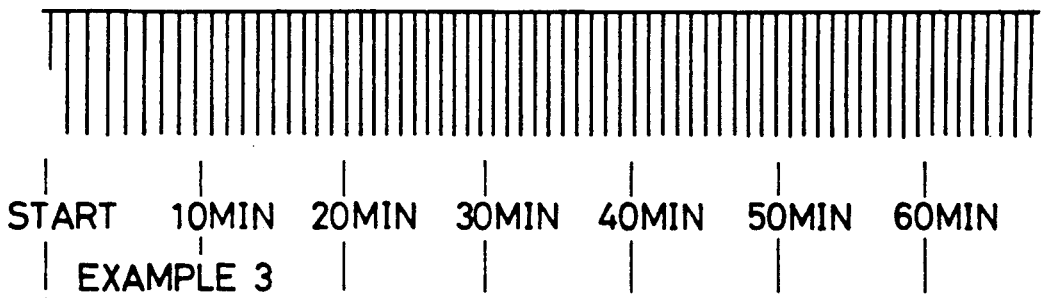
Figure 2B:
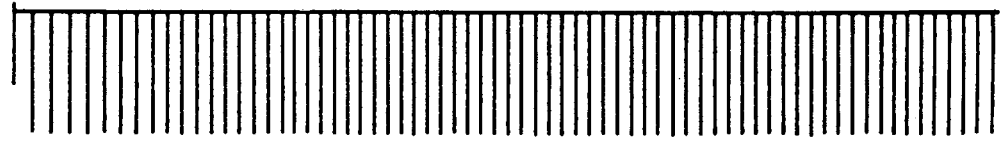
Figure 2B:
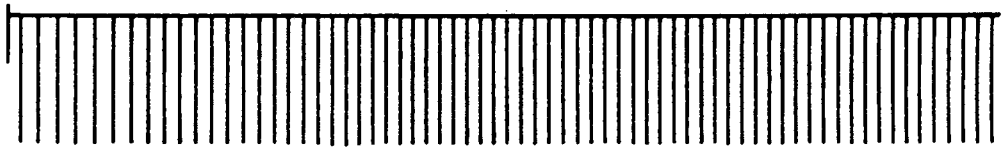
Figure 2B:
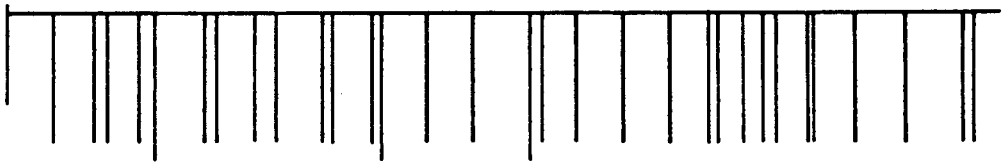

A syringe pump 20 as shown in FIG. 2(a) which is capable of pushing at a constant speed the body to be pushed which had been inserted into the syringe was used. The syringe 1 which had sucked water was engaged with the syringe pump 20. The quantity of injection of water from the syringe by the pushing head 21 of the syringe pump 20 was determined to be 1 ml/hour. The quantity of water injected from the syringe 1 was detected as a water drop of about 1/60 ml by a detector 22. The detected results were recorded by a recording device 24 via an amplifier 23 so that the diagram showing the signals was obtained as shown in FIG. 2(b). If the intervals between the signals shown in FIG. 2(b) are constant, it can be said that the quantity of injection per unit time period is constant and thereby there is no pulsation.

(7) Oil Bleed

The elution level of the plasticizer for rubber was tested. It was evaluated in such a manner that the state of the surface of the gasket at 23° C. for 7 days continued was visually observed.

The mixed components used in the embodiments and comparative examples were as follows:

(a) Hydrogen added derivative of styrene-budadiene block copolymer . . . "KRATON-G1651" manufactured by Shell Chemical (the Brookfield viscosity: 2000 cps. 77° F. in 20 wt % toluene solution)

(b) Plasticizer . . . "PW380" fluid paraffin manufactured by Idemitsu Kosan (kinetic viscosity at 40° C.: 381.6 cst)

(c-1) Polyethylene resin . . . Polyethylene-HD "JX-10" manufactured by Mitsubishi Petrochemical, Co. Ltd. (density: 0.956 g/cm$^3$, MFR: 190° C., 20 g/10 min)

(c-2) Polyethylene resin . . . Polyethylene-HD "JX-20" manufactured by Mitsubishi Petrochemical, Co. Ltd. (density: 0.964 g/cm$^3$, MFR: 190° C., 5.5 g/10 min)

(c-3) Polyethylene resin for comparative example . . . Polyethylene-HD "MS-30" manufactured by Mitsubishi Petrochemical, Co. Ltd. (density: 0.918 g/cm$^3$, MFR: 190° C., 20 g/10 min)

(c-4) Polypropylene resin for comparative example . . . "Mitsubishi Polypro BC5C" (MFR: 5 g/10 min)

(d) Hydrocarbon-type wax . . . Polyethylene wax "A-C Polyethylene, A-C8) manufactured by Allied Signal in the United States (dropping point: 116° C., Brooksfield viscosity: 400 cps. 140° C.)

Examples 1 to 10 and Comparative Examples 11 to 12

Phenol antioxidant "Iruganox 1010" was added by 0.1 parts by weight as a stabilizer to the mixtures shown in Table 1 with respect to 100 parts of the mixtures. Then, it was fused and kneaded by a two-shaft extruder of L/D=33 and a cylinder diameter of 45 mm at a predetermined temperature of 220° C. so that TPE pellet was obtained.

The 2 mm-thickness sheet to be tested and the gasket to be tested and having the peak diameter of 13.2 mm were manufactured by the above-described injection molding in which the pellet described above was used. The results of the various evaluations about the obtained sheets and gaskets are shown in Table 1.

Example 1 to 3, 7, and 8 are gaskets according to one embodiment. They exhibit a high stress under the same hardness, have a small permanent compression strain, and provide a satisfactory rubber elasticity. They exhibit satisfactory characteristics in respect of pulsation and oil bleed. In particular, Examples 1 to 3 are gaskets having particular mixture proportions. They excel in all respects, i.e., in formability, mold appearance, pulsation, and oil bleed.

Examples 4 to 6, 9, and 10 are gaskets according to another embodiment. They excel in all respects, i.e., in formability, mold appearance, pulsation, and oil bleed. In particular, Examples 4 to 6 are gaskets having a particular mixture proportion, and provide a particularly excellent mold appearance.

TABLE 1

|  |  | Example | | | | | | | | | | Comparative Example | |
|---|---|---|---|---|---|---|---|---|---|---|---|---|---|
|  |  | 1 | 2 | 3 | 4 | 5 | 6 | 7 | 8 | 9 | 10 | 11 | 12 |
| Mixture | a | 50 | 45 | 50 | 50 | 45 | 50 | 70 | 50 | 50 | 50 | 50 | 50 |
| (wt %) | b | 50 | 55 | 50 | 50 | 55 | 50 | 30 | 50 | 50 | 50 | 50 | 50 |
|  | c-1 |  | 17 | 13 | 13 | 15 | 13 |  |  |  |  |  |  |
|  | c-2 | 15 |  |  |  |  |  | 10 | 5 | 60 | 10 |  |  |
|  | c-3 |  |  |  |  |  |  |  |  |  |  | 40 |  |
|  | c-4 |  |  |  |  |  |  |  |  |  |  |  | 20 |
|  | d |  |  |  | 5 | 5 | 10 |  |  |  | 30 |  |  |
| JIS-A hardness |  | 65 | 57 | 55 | 60 | 70 | 65 | 63 | 37 | 98 NG | 82 | 69 | 68 |
| 300% stress (kgf/cm$^2$) |  | 36 | 35 | 31 | 35 | 38 | 37 | 48 | 26 | 93 | 53 | 32 | 22 |
| Permanent Compression strain (%) |  | 29 | 26 | 25 | 27 | 31 | 33 | 25 | 23 | — NG | 68 NG | 73 NG | 44 |
| Formability at molding |  | G | G | G | G | G | G | NG | NG | G | G | G | G |
| Mold appearance |  | G | G | G | E | E | E | — | — | G | G | G | G |
| Pulsation |  | G | G | G | G | G | G | G | G | G | G | G | NG |
| Oil bleed |  | G | G | G | G | G | G | G | G | G | G | NG | G |

E: Excellent G: Good NG: No Good

What is claimed is:

1. A gasket made of a composite comprising 100 parts by weight of (a) a hydrogen-added styrene-butadiene block copolymer and (b) a plasticizer, said 100 parts by weight being the total of 40 to 60 weight % of said (a) and 60 to 40 weight % of said (b), and 10 to 50 parts by weight of (c) a polyethylene resin having a density of 0.94 g/cm$^3$ or more.

2. The gasket according to claim 1, wherein the hydrogen-added styrene-butadiene block copolymer has a number average molecular weight of 5,000 to 1,000,000 and a ratio of its weight average molecular weight to its number average molecular weight of 10 or less.

3. The gasket according to claim 2, wherein the hydrogen-added styrene-butadiene block copolymer has a number average molecular weight of 10,000 to 800,000.

4. The gasket according to claim 2, wherein the hydrogen-added styrene-butadiene block copolymer has a number average molecular weight of 30,000 to 500,000.

5. The gasket according to claim 4, wherein the plasticizer is selected from the group consisting of a naphthene type plasticizer and a paraffin type plasticizer; the plasticizer having a coefficient of kinetic viscosity of 20 to 500 cst at 37.8° C., a pour point of −10° C. to −15° C. and a flash point of 170° C. to 300° C.

6. The gasket according to claim 5, wherein said 100 parts by weight is the total of 40 to 55 weight % of said (a) and 60 to 45 weight % of said (b); and said (c) is 10 to 30 parts by weight.

7. A gasket made of a composite comprising 100 parts by weight of (a) a hydrogen-added styrene-butadiene block copolymer and (b) a plasticizer, said 100 parts by weight being the total of 40 to 60 weight % of said (a) and 60 to 40 weight % of said (b), 10 to 50 parts by weight of (c) a polyethylene resin having a density of 0.94 g/cm$^3$ or more, and 2 to 20 parts by weight of (d) a hydrocarbon-type wax.

8. The gasket according to claim 7, wherein the hydrogen-added styrene-butadiene block copolymer has a number average molecular weight of 5,000 to 1,000,000 and a ratio of its weight average molecular weight to its number average molecular weight of 10 or less, and the plasticizer is selected from the group consisting of a naphthene type plasticizer and a paraffin type plasticizer, the plasticizer having a coefficient of kinetic viscosity of 20 to 500 cst at 37.8° C., a pour point of −10° C. to −15° C. and a flash point of 170° C. to 300° C.

9. The gasket according to claim 8, wherein the hydrogen-added styrene-butadiene block copolymer has a number average molecular weight of 10,000 to 800,000.

10. The gasket according to claim 8, wherein the hydrogen-added styrene-butadiene block copolymer has a number average molecular weight of 30,000 to 500,000.

11. The gasket according to claim 10 wherein the hydrocarbon-type wax is selected from the group consisting of a paraffin wax having a melting point of 40° C. to 100° C. and a viscosity of 1 to 30 cst at 100° C. and a polyethylene-type wax having a dropping point of 90° C. to 120° C. and a viscosity of 40 to 7,000 cps at 140° C.

12. The gasket according to claim 11, wherein said 100 parts by weight is the total of 40 to 55 weight % of said (a) and 60 to 45 weight % of said (b); said (c) is 10 to 30 parts by weight; and said (d) is 3 to 10 parts by weight.

13. A medical device comprising a cylindrical body and a gasket arranged in close contact with the inner surface of said cylindrical body and adapted to slide therein, said gasket being made of a composite comprising 100 parts by weight of (a) a hydrogen-added styrene-butadiene block copolymer and (b); a plasticizer, said 100 parts by weight being the total of 40 to 60 weight % of said (a) and 60 to 40 weight % of said (b), and 10 to 50 parts by weight of (c) a polyethylene resin having a density of 0.94 g/cm$^3$ or more.

14. The medical device according to claim 13, wherein the gasket further comprises 2 to 20 parts by weight of (d) a hydrocarbon-type wax.

15. The medical device according to claim 13, wherein the hydrogen-added styrene-butadiene block copolymer has a number average molecular weight of 5,000 to 1,000,000 and a ratio of its weight average molecular weight to its number average molecular weight of 10 or less, and the plasticizer is selected from the group consisting of a napthene type plasticizer and a paraffin type plasticizer, the plasticizer having a coefficient of kinetic viscosity of 20 to 500 cst at 37.8° C., a pour point of −10° C. to −15° C. and a flash point of 170° C. to 300° C.

16. The medical device according to claim 15, wherein the gasket further comprises 2 to 20 parts by weight of (d) a hydrocarbon-type wax.

17. The medical device according to claim 16, wherein the hydrocarbon-type wax is selected from the group consisting of a paraffin wax having a melting point of 40° C. to 100° C. and a viscosity of 1 to 30 cst at 100° C. and a polyethylene-type wax having a dropping point of 90° C. to 120° C. and a viscosity of 40 to 7,000 cps at 140° C.

18. The medical device according to claim 17, wherein said 100 parts by weight is the total of 40 to 55 weight % of said (a) and 60 to 45 weight % of said (b); said (c) is 10 to 30 parts by weight; and said (d) is 3 to 10 parts by weight.

* * * * *

UNITED STATES PATENT AND TRADEMARK OFFICE
CERTIFICATE OF CORRECTION

PATENT NO. : 5,061,247
DATED : October 29, 1991
INVENTOR(S) : AKAIKE et al It is certified that error appears in the above-identified patent and that said Letters Patent is hereby corrected as shown below:

Column 3, line 20, delete "softener", and insert --plasticizer--.

Col. 4, line 8, delete "Componet", and insert --Component D--.

Col. 6, line 38, delete "for rubber".

Signed and Sealed this

Thirteenth Day of September, 1994

Attest:

BRUCE LEHMAN

Attesting Officer

Commissioner of Patents and Trademarks